US008455616B2

(12) United States Patent
Ishizaka et al.

(10) Patent No.: US 8,455,616 B2
(45) Date of Patent: Jun. 4, 2013

(54) NUCLEAR TRANSLOCATION PEPTIDE

(75) Inventors: Yukihito Ishizaka, Tokyo (JP); Masakatsu Hasegawa, Nagoya (JP); Satoshi Nohara, Gifu (JP)

(73) Assignee: National Center for Global Health and Medicine, Tokyo (JP)

( * ) Notice: Subject to any disclaimer, the term of this patent is extended or adjusted under 35 U.S.C. 154(b) by 698 days.

(21) Appl. No.: 12/450,010

(22) PCT Filed: Mar. 6, 2008

(86) PCT No.: PCT/JP2008/054563
§ 371 (c)(1),
(2), (4) Date: Mar. 1, 2010

(87) PCT Pub. No.: WO2008/108505
PCT Pub. Date: Sep. 12, 2008

(65) Prior Publication Data
US 2010/0203611 A1     Aug. 12, 2010

(30) Foreign Application Priority Data
Mar. 7, 2007   (JP) ................................ 2007-057387

(51) Int. Cl.
*A61K 38/04*     (2006.01)
*A61K 38/08*     (2006.01)

(52) U.S. Cl.
USPC .......................... 530/328; 514/21.6; 514/21.8

(58) Field of Classification Search
USPC ................................. 530/328; 514/21.6, 21.7
See application file for complete search history.

(56) References Cited

U.S. PATENT DOCUMENTS 5,652,122 A     7/1997  Frankel et al.
2003/0077826 A1*  4/2003  Edelman et al. .............. 435/440

FOREIGN PATENT DOCUMENTS

WO           99/09412         2/1999
WO   WO 2005103654 A2 * 11/2005
WO     WO2005103654 A2 * 11/2005

OTHER PUBLICATIONS

Taguchi et. al. Nucleartrafficking of macromolecules by an oligopeptidederived from Vpr of human immunodeficiency virus type-1, vol. 320, Issue 1, p. 18-26, Jul. 16, 2004.*
International Search Report issued Jun. 3, 2008 in International (PCT) Application No. PCT/JP2008/054563.
Derossi D, Calvet S, Trembleau A, Brunissen A, Chassaing G, Prochiantz A. Cell internalization of the third helix of the Antennapedia homeodomain is receptor-independent. J Biol Chem. Jul. 26, 1996;271(30):18188-93. PubMed PMID: 8663410.
Elliott G, O'Hare P. Intercellular trafficking and protein delivery by a herpesvirus structural protein. Cell. Jan. 24, 1997;88(2):223-33. PubMed PMID: 9008163.
Hasegawa, M. Research on Peptide Addition to Magnetic Nano Particles and Optimization—Shared Research Report (2006), Groundbreaking Cutting-edge Medical Technology Development and Implementation Research Project (accompanied by English language translation).
Hasegawa, M. Research on Peptide Addition to Magnetic Nano Particles and Optimization—Shared Research Report (2007), Groundbreaking Cutting-edge Medical Technology Development and Implementation Research Project (accompanied by English language translation).
Mizoguchi I, Ooe Y, Hoshino S, Shimura M, Kasahara T, Kano S, Ohta T, Takaku F, Nakayama Y, Ishizaka Y. Improved gene expression in resting macrophages using an oligopeptide derived from Vpr of human immunodeficiency virus type-1. Biochem Biophys Res Commun. Dec. 23, 2005;338(3):1499-506. Epub Oct. 27, 2005. PubMed PMID: 16274667.
Mukai Y, Sugita T, Yamato T, Yamanada N, Shibata H, Imai S, Abe Y, Nagano K, Nomura T, Tsutsumi Y, Kamada H, Nakagawa S, Tsunoda S. Creation of novel Protein Transduction Domain (PTD) mutants by a phage display-based high-throughput screening system. Biol Pharm Bull. Aug. 2006;29(8):1570-4. PubMed PMID: 16880606.
Taguchi T, Shimura M, Osawa Y, Suzuki Y, Mizoguchi I, Niino K, Takaku F, Ishizaka Y. Nuclear trafficking of macromolecules by an oligopeptide derived from Vpr of human immunodeficiency virus type-1. Biochem Biophys Res Commun. Jul. 16, 2004;320(1):18-26. PubMed PMID: 15207696.
Vivès E, Brodin P, Lebleu B. A truncated HIV-1 Tat protein basic domain rapidly translocates through the plasma membrane and accumulates in the cell nucleus. J Biol Chem. Jun. 20, 1997;272(25):16010-7. PubMed PMID: 9188504.
Zhao M, Kircher MF, Josephson L, Weissleder R. Differential conjugation of tat peptide to superparamagnetic nanoparticles and its effect on cellular uptake. Bioconjug Chem. Jul.-Aug. 2002;13(4):840-4. PubMed PMID: 12121140.
Extended European Search Report issued Jul. 5, 2010 in corresponding European Application No. 08 73 8644.
Wang et al.; "Characterization of Leucine-Zipper-Like Domain in Vpr Protein of Human Immunodeficiency Virus Type 1"; Gene; 1996; vol. 178, No. 1-2; pp. 7-13.
Coeytaux et al.; "The Cationic Amphipathic α-Helix of HIV-1 Viral Protein R (Vpr) Binds to Nucleic Acids, Permeabilizes Membranes, and Efficiently Transfects Cells"; The Journal of Biological Chemistry; 2003; vol. 278, No. 20; pp. 18110-18116; USA.
Koita et al.; "Confirmation of Immunogenic Consensus Sequence HIV-1 T-Cell Epitopes in Bamako, Mali and Providence, Rhode Island"; Human Vaccines; 2006; vol. 2, No. 3; pp. 119-128.

* cited by examiner

*Primary Examiner* — Christina Bradley
*Assistant Examiner* — Jeanette Lieb
(74) *Attorney, Agent, or Firm* — Wenderoth, Lind & Ponack, L.L.P.

(57) ABSTRACT

The present invention provides a peptide comprising amino acid sequences R I, F I and R I G C and containing 25 or fewer amino acid residues, and capable of transporting a functional molecule into a cell, and also into a nucleus, more efficiently than a previous PTD.

7 Claims, 5 Drawing Sheets

NUCLEAR TRANSLOCATION PEPTIDE

This application is a U.S. national stage of International Application No. PCT/JP2008/054563 filed Mar. 6, 2008.

TECHNICAL FIELD

The present invention relates to a peptide capable of translocation into a cell and into a nucleus, and to conjugates of that peptide and a functional molecule.

BACKGROUND ART

Recently several peptides capable of translocation into a cell by passing through the cell membrane (Protein Transduction Domain, or PTD peptides) have been identified, and attempts have been made to utilize such PTD peptides widely as carriers to transport a protein, nucleic acid, polymer, or other functional molecule into cells.

Noteworthy examples of previously identified PTD peptides include a peptide originating in the Tat protein of HIV (E. Vives et al., J. Biological Chemistry, 272(25), 16010, (1997)), Penetratin (D. Derossi et al., J. Biological Chemistry, 271(30), 18188 (1996)), and VP22, a herpes simplex virus type 1 tegument protein (G. Elliot et al., Cell, 88, 223, (1997)).

The most well-known among the PTD peptides is the Tat peptide, and U.S. Pat. No. 5,652,122 discloses that intracellular transport of β-galactosidase or horseradish peroxidase was accomplished using the Tat peptide. In addition, Zhao et al. have reported performing intracellular imaging by MRI using a conjugate of the Tat peptide and superparamagnetic iron oxide nanoparticles (M. Zhao et al., Biconjugate Chem., 13, 840, (2002)).

Furthermore, Mukai et al. have reported that "YM-3," which exhibits cellular translocation capability approximately three times higher than that of the Tat peptide, was discovered during research to enhance the function of the Tat peptide (Y. Mukai et al., Biol. Pharm. Bull. 29(8), 1570, (2006)).

On the other hand, we previously identified C45D18, a peptide of 27 amino acid residues represented by SEQ ID NO: 16 (D T W A G V E A I I R I L Q Q L L F I H F R I G C R H) that has stronger translocation capability than a protein originating in Vpr, one of the accessory genes of HIV-1, and we have reported that conjugates of C45D18 and the aforementioned enzymatic proteins are peptides that can translocate not only into a cell, but also into a nucleus, and that the translocation capability thereof is greater than that of the Tat peptide (T. Taguchi et al., Biochem. Biophys. Res. Comm., 320, 18, (2004)). However, that document did not disclose the amino acid sequence necessary for achieving that translocation capability.

Thus several PTD proteins have been identified and modified, and attempts have been made to utilize them widely as a DDS (Drug Delivery System) carrier and the like, but they have not reached practical application on an industrial scale because the cellular translocation capability itself is still not fully understood.

DISCLOSURE OF THE INVENTION

An object of the present invention is to provide a peptide that can transport a functional molecule not only into a cell but also into a nucleus more efficiently than a previous PTD.

A further object of the present invention is to raise the amount of functional molecule translocated into a cell and into a nucleus to an industrially effective level thereby.

We originally synthesized the 20-amino acid residue peptide represented by the amino acid sequence of SEQ ID NO: 18 (R I L Q Q L L F I H F R I G C R H S R I) as a negative control during research utilizing the nuclear translocation capability of C45D18, but we surprisingly discovered that this peptide exhibits considerably greater translocation capability than C45D18. On the basis of this discovery we conducted diligent research to attain the aforementioned object of the present invention, and we identified a partial amino acid sequence of C45D18 that has considerably greater cellular translocation capability and nuclear translocation capability than previous PTD peptides, as well as lower cytotoxicity than C45D18, thus completing the present invention.

Thus, the present invention provides a peptide comprising amino acid sequences R I, F I and SEQ ID NO: 17 (R I G C) and containing 25 or fewer amino acid residues.

The peptide of the present invention can impart cellular and nuclear translocation capability to transport a protein, gene, sugar, or other polymer compound that cannot translocate intracellularly or intranuclearly on its own, and that capability is several times or even scores of times greater than when a conventional PDT peptide is used. As a result, through the utilization of the peptide of the present invention, practical application is now expected in fields heretofore impossible because of poor translocation function in the past.

The peptide of the present invention is also advantageous from the standpoint of safety when used in medical applications because it has less cytotoxicity than the C45D18 parent peptide.

Moreover, the peptide of the present invention has a small number of amino acid residues, and therefore has the advantage of lower cost in addition to lower cytotoxicity when utilized industrially.

Figure 1:
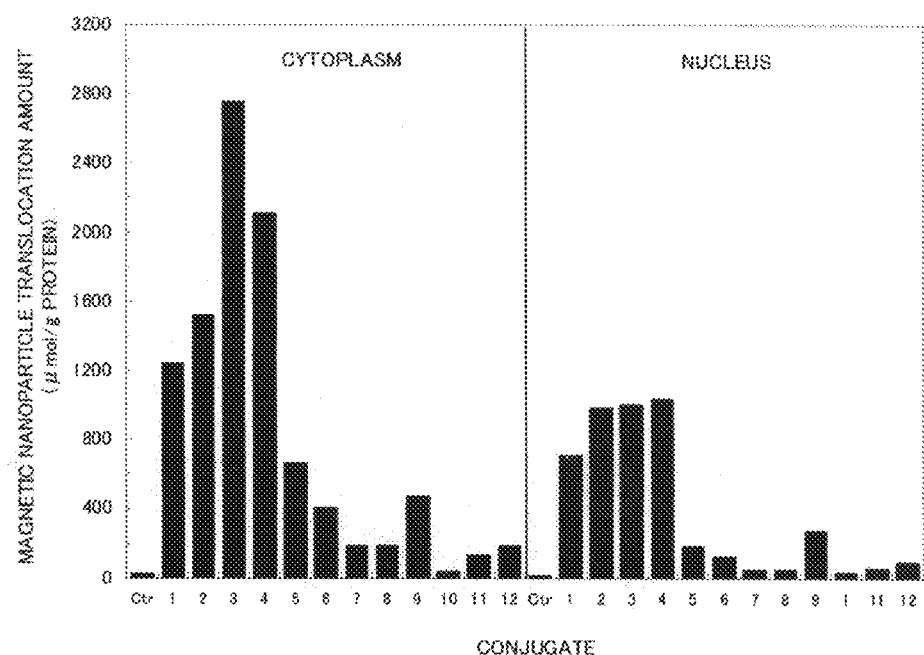
FIG. 1 is a graph showing the results of cellular and nuclear translocation capability tests of various peptide-CMDM conjugates in HeLa cells.

The peptide of the present invention is described below in greater detail.

BEST MODE FOR CARRYING OUT THE INVENTION

The peptide of the present invention (hereinafter referred to simply as the peptide) and process of producing the same, a listing of functional molecules that can be combined with the peptide, a method for synthesizing conjugates between the peptide and a functional molecule, evaluation of properties such as cellular and nuclear translocation capability of those conjugates, and targeted cells, etc., are described in order below.

In the following description the amino acid sequences are expressed in the form of the peptide numbers shown in Table 1 below for the sake of simplicity.

Correspondence between the Peptide Nos. of Table 1 and the SEQ ID NOs of the Sequence Listing is as follows:
Peptide No. 1 corresponds to SEQ ID NO: 18;
Peptide No. 2 corresponds to SEQ ID NO: 19;
Peptide No. 3 corresponds to SEQ ID NO: 20;
Peptide No. 4 corresponds to SEQ ID NO: 1;
Peptide No. 5 corresponds to SEQ ID NO: 3;
Peptide No. 6 corresponds to SEQ ID NO: 21;
Peptide No. 7 corresponds to SEQ ID NO: 22;
Peptide No. 8 corresponds to SEQ ID NO: 23;
Peptide No. 9 corresponds to SEQ ID NO: 16;
Peptide No. 10 corresponds to SEQ ID NO: 24;
Peptide No. 11 corresponds to SEQ ID NO: 25; and
Peptide No. 12 corresponds to SEQ ID NO: 26.

Peptide of the Present Invention

The peptide of the present invention is a peptide comprising the sequences R I, F I, and SEQ ID NO: 17 (R I G C) and containing 25 or fewer amino acid residues as the minimum necessary members exhibiting cellular and nuclear translocation capability. The preferred order of the above amino acid sequences in the peptide molecule, starting from the N-terminus, is R I, F I, and SEQ ID NO: 17 (R I G C). Ultimately, the above amino acid sequences are the minimum necessary sequences for exhibiting translocation capability, but it is possible to impart even higher translocation capability by adding other amino acid sequences before, after, or between the above sequences.

Accordingly, a peptide comprising amino acid sequences R I and SEQ ID NO: 27 (F I H F R I G C) in which H F has been inserted between sequences F I and SEQ ID NO: 17 (R I G C) and containing 25 or fewer amino acid residues is provided as a preferred mode of the present invention. Peptide 4 (R I F I H F R I G C) can be specifically noted as such a peptide, and this peptide exhibits a high level of translocation capability. Furthermore, the peptide represented by the amino acid sequence of SEQ ID NO: 2 (R I Xaa Q Q Xaa Xaa F I H F R I G C), for example, in which the sequence Xaa Q Q Xaa Xaa is inserted between R I and the sequence of SEQ ID NO: 27 (F I H F R I G C) in the above sequence (wherein Xaa can be any naturally occurring amino acid constituting proteins that function in mammals), and particularly the peptide represented by Peptide 3 (R I L Q Q L L F I H F R I G C) exhibits even higher translocation capability.

Such a peptide wherein specific amino acids are added to the minimum necessary sequence exhibits capability approximately ten times or even scores of times greater than conventional PDT peptides such as the Tat peptide or Penetratin.

Production Process

The peptide of the present invention can be produced by a previously known peptide synthesis method. The solid phase synthesis method (Marrifield, J. Am. Chem. Soc., 85, 2149-2154, 1963) can be noted as an example of such a peptide synthesis method. At present the peptide can be produced simply and in a relatively short period of time using an automated, general purpose peptide synthesizer based on those principles.

Additionally, the peptide can be produced using well-known means based on genetic engineering techniques such as those disclosed in exemplary reference documents (e.g., Methods in Enzymology, 154, 350, 367-382, 1987, etc.).

(b) List of Functional Molecules and Functional Particles

As noted above, because the peptide of the present invention has excellent cellular and nuclear translocation capability, it can be used as a vector, for example, by manufacturing a conjugate wherein the peptide is bonded to a functional molecule or functional particle, the conjugate is translocated into a cell or into a nucleus, and the function of that molecule or particle is then expressed therein. Selection can be made from an extremely broad range of molecules and particles that can be combined with the peptide.

Examples of the aforementioned functional molecule include biologically active substances such as nucleic acids (DNA, RNA, etc.), amino acids (proteins, peptides, etc.), lipids, sugars, and other polymer compounds, as well as functional compounds such as fluorescent substances, and the like. Examples of functional particles include magnetic particles, fluorescent particles, liposomes, and the like. These molecules and particles can be used alone or in combinations of two or more types thereof. Nanosize particles are particularly preferred. For the sake of convenience, functional molecules and functional particles are grouped together under the term functional molecule(s) below.

Representative functional molecules and functional particles are specifically described below, but the present invention is by no means limited thereto.

Nucleic Acids (DNA, RNA, etc.)

Generally, all types of nucleic acids such as plasmid DNA, mRNA, siRNA, etc., can be used without limitation as a nucleic acid that can be bonded to the peptide of the present invention. When using the peptide as a transformation vector, which is one application thereof, a mode wherein the function can be expressed within the cell can be used most suitably. For example, a preferred example of DNA is a DNA molecule that is transcribed in the transfected cell such that a biologically active substance produced therefrom expresses a desired function.

Examples of such of nucleic acids include genes for cytokines (e.g., TNF-α, interleukins, etc.), cancer antigen peptide genes (e.g., gp-100, MART-1, etc.), LDL receptor genes, etc. Genes used for the treatment of diabetes, atherosclerosis, Alzheimer's disease, and the like can also be noted.

Amino Acids (Proteins and Polypeptides)

Preferred amino acids that can be used for bonding with the peptide of the present invention are antibodies, enzymes, and the like that express some kind of intracellular biological activity after being transported into to a target cell.

Examples of such amino acids include proteins useable as an antigen that can be generally used because they induce cytotoxic T cells; cell cycle regulatory proteins (e.g., cyclin, cyclin-dependent kinases, etc.); antibodies (e.g., the HER2 antibody); enzymes (e.g., β-galactosidase, chloramphenicol transferase, etc.); immortal proteins (e.g., the SV40 large T antigen, telomerase, etc.); anti-apoptosis proteins (e.g., mutant p53, BclxL, etc.); and the like.

The method of bonding such amino acids to the peptide of the present invention is described in detail below in section "(c) Method of bonding the peptide of the present invention and a functional molecule," but it is also possible to synthesize an amino acid biologically utilizing bacteria, etc., such that the amino acid sequence of the peptide of the present invention is incorporated thereinto beforehand. The bonding site can be either on the N-terminal or C-terminal side.

One example of a method for obtaining an amino acid wherein the amino acid sequence of the peptide of the present invention has been incorporated thereinto beforehand involves inserting DNA encoding the amino acid sequence of the amino acid to be transported and the amino acid sequence of the peptide of the present invention into a plasmid generally used as an expression vector, and then obtaining the product thereof through expression in E. coli, etc. In accordance with this method it is possible to impart intracellular transport capability concurrently with obtaining the target amino acid, and this is advantageous from the aspect of cost when moving to practical application. The present invention also includes an amino acid inserted with the peptide of the present invention and obtained in such a manner, as well as the process for producing the same.

Magnetic Particles

Depending on their forms, properties, etc., there is a wide variety of versatile magnetic particles available as magnetic particles that can be used for bonding with the peptide of the present invention. A preferred form suitable for use with the peptide is a so-called magnetic nanosize particle that has excellent biocompatibility and a total diameter within a nanometer order (nanosize), but the magnetic particles herein are not limited thereto.

The particles disclosed in the descriptions of Japanese Examined Patent Publication (Kokoku) No. S59-13521, Japanese Patent No. 2939336, U.S. Pat. No. 4,452,773 and the like can be noted as examples of such magnetic nanoparticles, and these have reached widespread practical application as MRI imaging agents and for the magnetic separation of cells.

Among the above, the carboxyalkyl polysaccharide-magnetic metal oxides, and particularly carboxymethyl dextran magnetite (hereinafter CMDM), which are disclosed in Japanese Patent No. 2726520, have a functional group that can be used for bonding with another molecule on the surface of the particle, and can be most suitably used in the present invention. The citation of that patent publication is provided herein in place of a detailed explanation of the specific method of synthesis.

The aforementioned magnetic particles generally can have an overall diameter in the range of 1 to 500 nm, preferably 1 to 200 nm, and even more preferably 1 to 150 nm, depending on the use thereof, and can be suitably selected in accordance with that application. The overall diameter herein is a value obtained by measurement with a laser light scattering particle size distribution analyzer.

Furthermore, the $T_2$ relaxation, for example, can be noted as an indicator of the magnetic strength of the magnetic particles. Preferably this numerical value is as high as possible from the standpoint of detection sensitivity in MRI and heat generating capability in thermotherapy, and normally a value within the range of 1 to 1000 $(mM·sec)^{-1}$, preferably 20 to 1000 $(mM·sec)^{-1}$ and even more preferably 50 to 1000 $(mM·sec)^{-1}$ is suitable. Herein the $T_2$ relaxation is a value measured at 0.47 T with a pulse NMR device.

Liposomes

A previously known liposome can generally be used as a liposome that can bond with the peptide of the present invention. For example, when used as a drug delivery system (DDS), which is one application of the peptide of the present invention, it is preferable for the liposome to have a suitable overall diameter large enough to encapsulate the drug, and in particular, it is preferable for the liposome to be designed such that the liposome membrane can be destroyed as needed after completing delivery into the cell, but the liposomes herein are not limited thereto. An example of such a liposome is the thermal sensitive liposome disclosed in Japanese Patent Application Laid-open No. 2006-306784. The citation of that patent publication is used herein in place of a detailed explanation of specific method of synthesis and the desired properties.

Fluorescent Particles

The fluorescent particles that can bond with the peptide of the present invention are not particularly limited herein with respect to fluorescence wavelength and shape, but with respect to size they obviously cannot exceed the size of the cell, and preferably they will be on a nanometer order or less. Moreover, those with good biocompatibility are especially preferred. Examples of such particles include, for example, quantum dots. Among these, the "Qdot®" developed by the American company Quantum Dot Corporation is the most well known and can be noted as one example thereof, but the fluorescent particles herein are not limited thereto.

(c) Method of Bonding the Peptide of the Present Invention and a Functional Molecule (Process of Producing the Conjugate)

Bonding between the peptide of the present invention and the functional molecule can be carried out directly, or it can be carried out indirectly via a linker molecule. In addition, depending on the functional molecule, bonding can be carried out merely by mixing the functional molecule with the peptide of the present invention. In general, the bonding can be carried out by a previously known method, and more specifically, it can be carried out either directly or, when direct bonding is impossible, indirectly via a linker molecule by a chemical bonding method utilizing a functional group that is present either on the end of or inside the biological molecule serving as the functional molecule. Examples of the chemical bonding type in that process include covalent bonds such as an amide bond, ester bond, thioester bond, ether bond, thioether bond, and S—S bond; and non-covalent bonds such as an ionic bond, electrostatic attraction, van der Vaals attraction, hydrogen bond, and the like. However, the bonding type herein is not limited thereto. The aforementioned linker molecule is not particularly limited herein provided it has a reactive group on each end, and is a molecule with a structure that can link two other molecules. Examples of reactive groups include a maleimide group, N-succinimide ester group, epoxy group, and avidin group, but the reactive group herein is not limited thereto.

Bonding between the peptide and liposome or magnetic particle can be carried out directly, but because relatively few liposomes or magnetic particles have a reactive group that can be used for direct bonding on the surface thereof, normally bonding will be carried out indirectly via some kind of linker molecule. For bonding between the aforementioned magnetic nanoparticles and the peptide, a most suitable method is one wherein CMDM is used as the magnetic nanoparticle, a linker is introduced thereon using the carboxyl groups on the surface thereof, and the peptide is bonded to the other end of the linker.

As noted above, combinations of the peptide and functional molecule cover a wide range, and the bonding method thereof cannot be determined unequivocally. By considering the relationship between structure and activity, a person skilled in the art can easily decide empirically on a bonding method that is suitable for each combination of the peptide and a functional molecule from among previously known bonding methods.

(d) Properties of the Conjugate (Including Cellular and Nuclear Translocation Capability)

Properties that should be exhibited by the conjugate of the peptide of the present invention and the functional molecule are not particularly limited herein provided they do not interfere with cellular and nuclear translocation. In this case, an example of a property that can interfere with translocation is size, and more specifically the overall diameter of the conjugate can be noted. The mechanism of cellular and nuclear translocation of the peptide of the present invention is believed to depend on macropinocytosis, and if the overall diameter of the conjugate is small, that is not a problem, but if it is too large, there is a chance that the conjugate may not be able to pass through the cell membrane and nuclear membrane. Therefore, preferably the overall diameter of the above conjugate is normally 5 to 500 nm, particularly 5 to 200 nm, and even more particularly 5 to 150 nm.

The preferred peptide-magnetic nanoparticle conjugate of the present invention that has been prepared in the manner described above can have the desirable properties noted below.

Depending on the manufacturing conditions, the above conjugate will preferably have roughly the same properties as those of generally used magnetic nanoparticles and depending on the use, it will normally have an overall diameter within a range of 5 to 500 nm, preferably 5 to 200 nm, and more preferably 5 to 150 nm.

As noted above, it is preferable for the $T_2$ relaxation to be as high as possible, and it can lie within a range of normally 1 to 1000 $(mM \cdot sec)^{-1}$, preferably 20 to 1000 $(mM \cdot sec)^{-1}$ and even more preferably 50 to 1000 $(mM \cdot sec)^{-1}$.

The content of the peptide in the peptide-functional molecule conjugate described above can vary depending on the use of the conjugate, size of the functional molecule, and the like, but it is preferred that the function of the peptide can be fully realized, and that the content thereof be as small as possible. Therefore, the content of the peptide per functional molecule can lie within a range of normally 1 to 30, preferably 1 to 25, and more preferably 1 to 20.

Amount of Cellular and Nuclear Translocation

With respect to the amount of cellular and nuclear translocation of the aforementioned peptide-magnetic nanoparticle conjugate, the translocation capability of the peptide of the present invention can be compared with that of a previous PTD by adding the conjugate to cultured cells, separating and recovering the cytoplasm and nuclei after letting the culture stand for a set period of time, measuring the $T_2$ relaxation time by NMR, and measuring the amount of magnetic nanoparticles taken up by the cells.

Targeted Cells

The targeted cells into which the peptide-functional molecule conjugate of the present invention can translocate are not particularly limited herein provided they are cells that do not have a cell wall. The cells can be either dividing or non-dividing types, and can be selected as desired depending on the use. For example, when the peptide-functional molecule conjugate of the present invention is used in basic research as a gene transfer agent, a wide range of various types of normal cells, tumor cells, or immortal cells ranging from bacteria to insects to mammals can be noted. When applied to the treatment of human diseases, examples include various types of normal cells, tumor cells, or immortal cells (e.g., CHO, COS, etc.), and preferably human normal cells, tumor cells, or immortal cells (e.g., HeLa, Huh-7, 293, MCF-7, neurons, nonadherent blood cells, etc.)

Applications of the Conjugate

A functional molecule conjugate wherein the peptide of the present invention has been introduced will have considerably enhanced cellular and even nuclear translocation capability, and therefore based on this translocation capability it can be used as a vector, can be used to transport a biologically active substance into a cell or into a nucleus, and can be used in a variety of applications depending on the nature of the functional molecule. For example, if a gene is used as the functional molecule, the conjugate can be used for gene transfer, or if a cytotoxic molecule is used, the conjugate can be used as a DDS. However, the applications of the peptide of the present invention are not limited thereto, and it can be used extensively provided the mode of application is one utilizing the function thereof as a cellular or nuclear vector for various kinds of functional molecules.

On such an occasion, the peptide of the present invention can be combined and used with a different cellular translocation molecule. For example, by bonding the peptide of the present invention to a positively charged molecule that functions as a gene transduction vector, it becomes possible to transfer a gene into a non-dividing cell. Alternatively, by bonding the peptide of the present invention onto the surface of a virus particle used for gene expression, it becomes possible to deliver the virus particle directly into the nucleus and express an exogenous gene thereby.

On the other hand, if the peptide of the present invention is combined with the aforementioned magnetic nanoparticle capable of being inductively heated by exposure to a high-frequency magnetic field to make a magnetic nanoparticle conjugate, the magnetic particle conjugate can generate heat not only in the cytoplasm but also the nucleus, and can be applied to thermotherapy. In addition, because the aforementioned magnetic nanoparticle conjugate vibrates as it is heated, it can impart mechanical cytotoxicity whereby DNA in the nucleus and nuclear membrane function are damaged. Moreover, the present invention provides a cell treatment method wherein cells treated with the magnetic nanoparticle conjugate are exposed to a high-frequency magnetic field.

EXAMPLES

The present invention is described in greater detail below through examples, comparative examples, and experimental examples.

CMDM and large particle CMDM that were synthesized following the method disclosed in Japanese Patent No. 2726520 and exhibit the properties shown in 1) and 2) below were used in the examples and comparative examples.

1) CMDM Properties

Iron concentration: 44.2 mg/mL (iron yield 83%), magnetic iron oxide particle size: 5.1 nm, overall particle size: 40 nm, CMD/iron weight ratio: 0.7, $T_1$ relaxation: 32 $(mM \cdot sec)^{-1}$, $T_2$ relaxation: 121 $(mM \cdot sec)^{-1}$.

2) Large Particle CMDM Properties

Iron concentration: 20.4 mg/mL overall particle size: 75 nm, CMD/iron weight ratio: 0.6, $T_1$ relaxation: 38 $(mM \cdot sec)^{-1}$, $T_2$ relaxation: 312 $(mM \cdot sec)^{-1}$.

Example 1

Synthesis of LR20 (Peptide 1)

A peptide synthesizer (Pioneer type from Applied Biosystems) based on the principles of solid phase synthesis was used, and automatic synthesis was carried out by programming the synthesizer for the 20 amino acid residue sequence of the above peptide LR20 and providing the set of amino acid reagents necessary for peptide synthesis of peptide LR20. After synthesis was completed, the peptide was separated from the carrier resin using TFA, and after the resin was removed, ether was added, followed by centrifugation (3000 rpm for 5 min), and the precipitated peptide was lyophilized to obtain the peptide. The molecular weight of the resulting peptide was measured by mass spectrometry (Voyager RP type from Applied Biosystems), the purity was measured from the peak area of HPLC analysis (Kanto Chemical Co., Ltd., Mightysil RP-18GP column, detection wavelength: 220 nm, eluent: 0.1% TFA/$H_2O$), and it was confirmed that the resulting peptide was the LR20 peptide.

Mass spectrometry results: measured molecular weight 2506.7 (theoretical molecular weight: 2507.3), HPLC analysis: retention time 22.825 min (93.6%).

Example 2

Synthesis of LR20-CMDM (1) A reaction was carried out at room temperature by sequentially adding 8 mL of a 0.2 M sodium phosphate buffer solution containing 623 mg of 1-ethyl-3-(3-dimethylaminopropyl) carbodiimide HCl (hereinafter, EDC), 187 mg of N-hydroxy succinimide (hereinafter, NHS), and 22 mg N-ethyl amino maleimide•trifluoroacetate to 8 mL of CMDM (iron concentration: 20 mg/mL) with an overall diameter of 40 nm. After 20 h had elapsed, ultrafiltration (molecular cutoff 50 kDa) was performed, and unnecessary reagents were removed to obtain 28 mL of linker-bonded CMDM aqueous solution.

(2) A reaction was carried out at room temperature by adding 9.8 mg of LR20 (Peptide 1) to 10 mL of the linker-bonded CMDM aqueous solution obtained in above (1). After 20 h had elapsed, ultrafiltration (molecular cutoff 50 kDa) was performed, and the unbound peptide was recovered and quantified. The supernatant was diluted with water, 1.0 mg of cysteine was added, and a reaction was carried out at room temperature. After 20 h had elapsed, ultrafiltration (molecular cutoff 50 kDa) was performed, and the supernatant was diluted with 8 mL of 0.1 M sodium phosphate buffer to obtain a hydrosol of LR20-CMDM (Conjugate 1).

Iron concentration: 7.6 mg/mL, CMD/iron weight ratio: 0.60, overall particle diameter: 49 nm (PH9), $T_1$ relaxation: 28 $(mM \cdot sec)^{-1}$, $T_2$ relaxation: 115 $(mM \cdot sec)^{-1}$, number of peptide bonds per magnetic nanoparticle: 10.0.

Example 3

Synthesis of LR17 (Peptide 2)

Synthesis and analysis were performed in the same manner as in Example 1 except for programming of the sequence and providing the set of necessary amino acids to match the sequence of LR17, and the LR17 peptide was obtained thereby.

Mass spectrometry results: measured molecular weight 2150.25 (theoretical molecular weight: 2150.670), HPLC analysis: retention time 19.000 min (100.0%).

Example 4

Synthesis of LR17-CMDM

A treatment was performed in the same manner as Example 2 except that 8.4 mg of LR17 (Peptide 2) was used as the added peptide to obtain a hydrosol of LR17-CMDM (Conjugate 2).

Iron concentration: 6.7 mg/mL, CMD/iron weight ratio: 0.58, number of peptide bonds per magnetic nanoparticle: 11.4.

Example 5

Synthesis of LR15 (Peptide 3)

Synthesis and analysis were performed in the same manner as in Example 1 except for programming of the sequence and providing the set of necessary amino acids to match the sequence of LR15, and the LR15 peptide was obtained thereby.

Mass spectrometry results: measured molecular weight 1857.47 (theoretical molecular weight: 1857.340), HPLC analysis: retention time 19.600 min (100.0%).

Example 6

Synthesis of LR15-CMDM

A treatment was performed in the same manner as Example 2 except that 7.2 mg of LR15 (Peptide 3) was used as the added peptide to obtain a hydrosol of LR15-CMDM (Conjugate 3).

Iron concentration: 7.5 mg/mL, CMD/iron weight ratio: 0.60, number of peptide bonds per magnetic nanoparticle: 10.0.

Example 7

Synthesis of LR15DL (Peptide 4)

Synthesis and analysis were performed in the same manner as in Example 1 except for programming of the sequence and providing the set of necessary amino acids to match the sequence of LR15DL, and the LR15DL peptide was obtained thereby.

Mass spectrometry results: measured molecular weight 1261.97 (theoretical molecular weight: 1261.575), HPLC analysis: retention time 16.992 min (97.7%).

Example 8

Synthesis of LR15DL-CMDM

A treatment was performed in the same manner as Example 2 except that 2.5 mg of LR15DL (Peptide 4) was used as the added peptide to obtain a hydrosol of LR15DL-CMDM (Conjugate 4).

Iron concentration: 7.6 mg/mL, CMD/iron weight ratio: 0.55, number of peptide bonds per magnetic nanoparticle: 10.1.

Example 9

Synthesis of LR8DHF (Peptide 5)

Synthesis and analysis were performed in the same manner as in Example 1 except for programming of the sequence and providing the set of necessary amino acids to match the sequence of LR8DHF, and the LR18DHF peptide was obtained thereby.

Mass spectrometry results: measured molecular weight 977.26 (theoretical molecular weight: 977.27), HPLC analysis: retention time 18.950 min (98.5%).

Example 10

Synthesis of LR8DHF-CMDM

A treatment was performed in the same manner as Example 2 except that 3.8 mg of LR8DHF (Peptide 5) was used as the added peptide to obtain a hydrosol of LR8DHF-CMDM (Conjugate 5).

Iron concentration: 7.5 mg/mL, CMD/iron weight ratio: 0.52, number of peptide bonds per magnetic nanoparticle: 10.1.

Comparative Example 1

Synthesis of LR11 (Peptide 6) with Additional GGC

Synthesis and analysis were performed in the same manner as in Example 1 except for programming of the sequence and providing the set of necessary amino acids to match the sequence of LR11+GGC, and the LR11 peptide (with additional GGC) was obtained thereby.

Mass spectrometry results: measured molecular weight 1645.05 (theoretical molecular weight: 1645.05), HPLC analysis: retention time 19.308 min (94.1%).

Comparative Example 2

Synthesis of LR11-CMDM

A treatment was performed in the same manner as Example 2 except that 6.4 mg of LR11 (Peptide 6) having GGC added to the C-terminus thereof was used as the added peptide and that the peptide was dissolved in DSMO when added, to obtain a hydrosol of LR11-CMDM (Conjugate 6).

Iron concentration: 7.5 mg/mL, CMD/iron weight ratio: 0.61, number of peptide bonds per magnetic nanoparticle: 10.4.

Comparative Example 3

Synthesis of LR8DHFRI (Peptide 7)

Synthesis and analysis were performed in the same manner as in Example 1 except for programming of the sequence and providing the set of necessary amino acids to match the sequence of LR8DHFRI, and the LR8DHFRI peptide was obtained thereby.

Mass spectrometry results: measured molecular weight 708.98 (theoretical molecular weight: 707.91), HPLC analysis: retention time 16.88 min (96.1%).

Comparative Example 4

Synthesis of LR8DHFRI-CMDM

A treatment was performed in the same manner as Example 2 except that 4.5 mg of LR8DHFRI (Peptide 7) was used as the added peptide to obtain a hydrosol of LR8DHFRI-CMDM (Conjugate 7).

Iron concentration: 7.1 mg/mL, number of peptide bonds per magnetic nanoparticle: 10.3.

Comparative Example 5

Synthesis of LR8DRUHF (Peptide 8)

Synthesis and analysis were performed in the same manner as in Example 1 except for programming of the sequence and providing the set of necessary amino acids to match the sequence of LR8DRIHF, and the LR8DRIHF peptide was obtained thereby.

Mass spectrometry results: measured molecular weight 708.40 (theoretical molecular weight: 707.91), HPLC measured purity: 100.0%.

Comparative Example 6

Synthesis of LR8DRIHF-CMDM

A treatment was performed in the same manner as Example 2 except that 4.5 mg of LR8DRIHF (Peptide 8) was used as the added peptide to obtain a hydrosol of LR8DRIHF-CMDM (Conjugate 8).

Iron concentration: 6.6 mg/mL, number of peptide bonds per magnetic nanoparticle: 10.7.

Comparative Example 7

Synthesis of C45D18 (Peptide 9)

Synthesis and analysis were performed in the same manner as in Example 1 except for programming of the sequence and providing the set of necessary amino acids to match the sequence of C45D18, and the C45D18 peptide was obtained thereby.

Mass spectrometry results: measured molecular weight 3207.1.

Comparative Example 8

Synthesis of C45D18-CMDM

A treatment was performed in the same manner as Example 2 except that 12.5 mg of C45D18 (Peptide 9) was used as the added peptide to obtain a hydrosol of C45D18-CMDM (Conjugate 9).

Iron concentration: 7.4 mg/mL, CMD/iron weight ratio: 0.58, overall particle diameter: 46 nm (PH9), $T_1$ relaxation: 29 $(mM \cdot sec)^{-1}$, $T_2$ relaxation: 117 $(mM \cdot sec)^{-1}$, number of peptide bonds per magnetic nanoparticle: 10.3.

Comparative Example 9

Synthesis of Penetratin (Peptide 10) with Additional GGC

Synthesis and analysis were performed in the same manner as in Example 1 except for programming of the sequence and providing the set of necessary amino acids to match the sequence of Penetratin+GGC, and the Penetratin peptide (with additional GGC) was obtained thereby.

Mass spectrometry results: measured molecular weight 2464.38 (theoretical molecular weight: 2464.03), HPLC analysis: retention time 19.28 min (99.5%).

Comparative Example 10

Synthesis of Penetratin-CMDM

A treatment was performed in the same manner as Example 2 except that 9.5 mg of Penetratin (Peptide 10) having GGC added to the C-terminus thereof was used as the added peptide, and a hydrosol of Penetratin-CMDM (Conjugate 10) was obtained.

Iron concentration: 7.7 mg/mL, CMD/iron weight ratio: 0.60, number of peptide bonds per magnetic nanoparticle: 9.8.

Comparative Example 11

Synthesis of tat (Peptide 11) with Additional GGC

Synthesis and analysis were performed in the same manner as in Example 1 except for programming of the sequence and providing the set of necessary amino acids to match the sequence of tat+GGC, and the tat peptide (with additional GGC) was obtained thereby.

Mass spectrometry results: measured molecular weight 1834.3.

Comparative Example 12

Synthesis of tat Peptide-CMDM

A treatment was performed in the same manner as Example 2 except that 7.0 mg of tat peptide (Peptide 11) having GGC added to the C-terminus thereof was used as the added peptide, and a hydrosol of tat peptide-CMDM (Conjugate 11) was obtained.

Iron concentration: 7.3 mg/mL, CMD/iron weight ratio: 0.57, number of peptide bonds per magnetic nanoparticle: 10.1.

Comparative Example 13

Synthesis of YM-3 (Peptide 12) with Additional GGC

Synthesis and analysis were performed in the same manner as in Example 1 except for programming of the sequence and providing the set of necessary amino acids to match the sequence of YM-3+GGC, and the YM-3 peptide (with additional GGC) was obtained thereby.

Mass spectrometry results: measured molecular weight 1777.78 (theoretical molecular weight: 1777.10), HPLC analysis: retention time 18.36 min (99.1%).

Comparative Example 14

Synthesis of YM-3-CMDM

A treatment was performed in the same manner as Example 2 except that 7.0 mg of YM-3 (Peptide 12) having GGC added to the C-terminus thereof was used as the added peptide, and a hydrosol of YM-3-CMDM (Conjugate 12) was obtained.

Iron concentration: 7.3 mg/mL, CMD/iron weight ratio: 0.59, number of peptide bonds per magnetic nanoparticle: 10.6.

Example 11

Synthesis of LR17-Large Particle CMDM

A treatment was performed in the same manner as Example 4 except that CMDM particles with an overall diameter of 75 nm were used as the CMDM and a hydrosol of LR17-large particle CMDM (Conjugate 13) was obtained.

Iron concentration: 7.5 mg/mL, CMD/iron weight ratio: 0.34, number of peptide bonds per magnetic nanoparticle: 16.2.

Example 12

Synthesis of LR15DL-Qdot

A reaction was carried out at 25° C. for 30 min by adding 7 µg of sulfo-SMCC to 20 µL of Qdot ITK705™. The reaction product was subjected to size exclusion chromatography (Sephadex G50, eluent 0.01 M-PBS), and unnecessary reagents were removed. Finally, 2 µg of LR15DL were added, and reacted at 25° C. to obtain a hydrosol of LR15DL-Qdot (Conjugate 14).

Example 13

Synthesis of LR15DL-EGFP

LR15DL (Peptide 4) and EGFP (Enhanced Green Fluorescent Protein) were mixed at molar ratios of 1:1, 3:1, and 10:1, and incubated for 1 h at 4° C. to obtain three types of LR15DL-EGFP with different amounts of bonding (Conjugate 15).

Example 14

Preparation of His-tagged-LR15DL-EGFP chimeric protein

The pET15b plasmid was used as expression plasmid DNA expressing six histidine residues as a tag. First a DNA sequence encoding EGFP was inserted into the vector. Next a recombinant was formed wherein the DNA sequence of SEQ ID NO: 29 encoding LR15DL (AGG ATC TTC ATC CAC TTC CGG ATC GGC TGC) was inserted at the NdeI-BamHI site in this DNA. BL12 *E. coli* (Novagen) cells for expression of recombinant proteins were transfected with each expression plasmid DNA, and the DNA was expressed thereby. The resulting crude protein was purified by an affinity column (Invitrogen, model R901-15) surface-treated with nickel, which undergoes specific chelate binding with the His tag, to obtain the $(His)_6$-EGFP peptide alone and the $(His)_6$-LR15DL-EGFP chimeric protein (Conjugate 16).

Experimental Example 1

Cellular and Nuclear Translocation Capability of Magnetic Particles in HeLa Cells Cellular and nuclear translocation testing in HeLa cells was conducted on the conjugates synthesized in Examples 1 to 11 and Comparative Examples 1 to 15. The following test method was used.

First 3 mL of each of the peptide-magnetic particle conjugates obtained in Examples 1 to 11 and Comparative Examples 1 to 15 (iron concentration adjusted to 0.7 mg/mL with liquid culture medium) was added to $2 \times 10^6$ HeLa cells wherein the cell cycle had been arrested with thymidine. After 18 h of exposure, the cells were washed with PBS and recovered, and centrifugal separation (2000 rpm for 5 min) was performed to precipitate the cells into pellets. After the cells were resuspended by adding 700 mL of PBS, they were lysed using a Dounce homogenizer and centrifuged (2000 rpm for 5 min) into pellets. The supernatant was the cytoplasmic fraction and the pellets were the nuclear fraction (the pellets were sonicated after adding 0.5% Triton X-100/PBS solution). Then the $T_2$ relaxation time of each resulting fraction was measured by NMR. Concurrently, the protein concentration of each fraction was measured by BSA protein assay.

Figure 2:
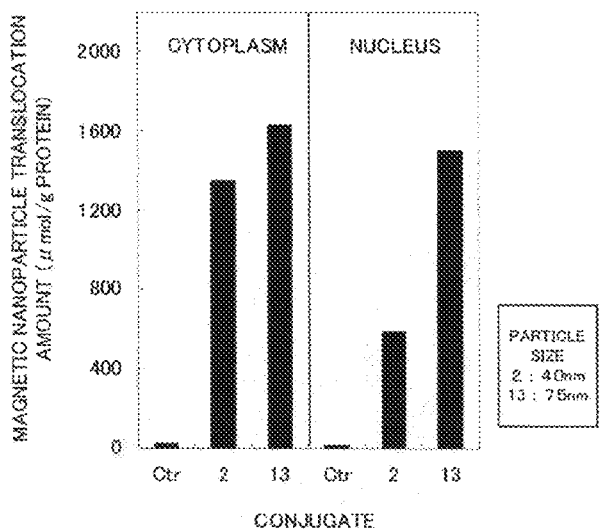
FIG. 2 is a graph showing the results of tests comparing cellular and nuclear translocation capability depending on differences in particle size of the LR17-CMDM conjugates in HeLa cells.

Because a fixed relation is established between $T_2$ relaxation time and magnetic substance concentration, the magnetic substance concentration can be calculated by assuming that the $T_2$ relaxation of the sample is the same before and after the test. The calculated concentration was corrected further using the protein concentration. FIGS. 1 and 2 show the results.

As can clearly be seen from the results of FIG. 1, Conjugates 1 to 5 comprising the peptide obtained according to the present invention exhibited several to scores of times greater translocation capability than Conjugates 9 to 12 comprising previous peptides.

Among the conjugates containing the peptide of the present invention, because the translocation capability increases in order from Conjugate 1 to 3, it is shown that the C-terminal amino acid sequence of SEQ ID NO: 30 (R H S R I) is a part that is unnecessary for cellular and nuclear translocation because the peptide of Peptide 3, which lacks that part, had the best cellular and nuclear translocation capability. The result for Conjugate 4 showed that although the cellular translocation decreased somewhat when amino acid sequence of SEQ ID NO: 31 (L Q Q L L) was removed, nuclear translocation was sufficiently maintained. Furthermore, the results for Conjugates 5 to 8 indicated that the amino acid sequences R I and F I and SEQ ID NO: 17 (R I G C) in Peptide 5 are the minimum necessary sequence for cellular and nuclear translocation capability.

The results from FIG. 2 indicated that even when the particle size of the translocated CMDM was increased, the amount of cellular translocation did not change and was controlled by the amount of peptide that was introduced.

Experimental Example 2

Cellular and Nuclear Translocation Capability of Magnetic Particles in Neurons

Cellular and nuclear translocation testing was performed in neurons for Conjugates 1, 2, and 12 by the same method as in Experimental Example 1 except that neurons prepared from mouse fetal cerebral cortex were used as the targeted cells. The results are shown in FIG. 3.

Figure 3:
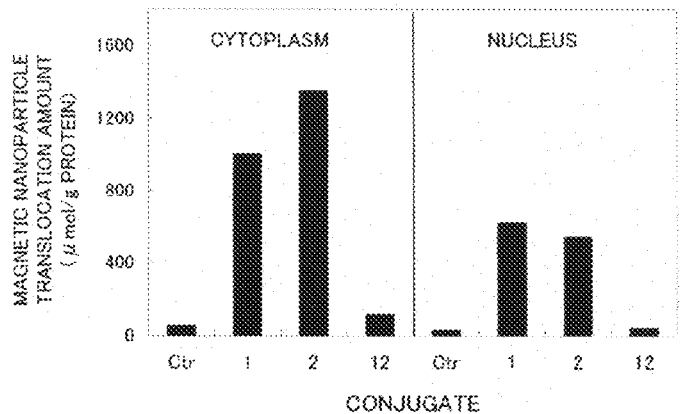
FIG. 3 is a graph showing the cellular and nuclear translocation capability tests of various peptide-CMDM conjugates in neurons.

The results of FIG. 3 show that the peptide of the present invention exhibits translocation capability several times greater than that of previous peptides.

Experimental Example 3

Figure 4:
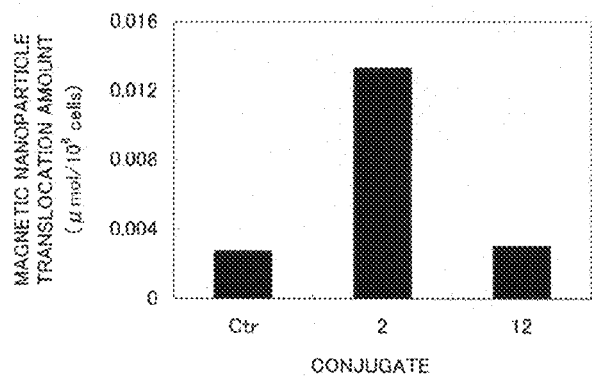
FIG. 4 is a graph showing the results of cellular translocation capability tests of various peptide-CMDM conjugates in peripheral mononuclear cells.

Cellular Translocation Capability of Magnetic Particles in Peripheral Mononuclear Cells Conjugates 2 and 12 (iron concentration adjusted to 0.7 mg/mL with liquid culture medium) were added to $2 \times 10^6$ human peripheral mononuclear cells. The human mononuclear cells were prepared from blood of test subjects using Lymphoprep (AXIS-SHIELD plc). After 18 h the cells were recovered, washed 3 times with PBS, suspended in 0.6 mL of PBS containing 1% Triton X-100, and sonicated. The $T_2$ relaxation time of the resulting samples was measured by NMR and the magnetic substance concentration was calculated. FIG. 4 shows the results.

The results of FIG. 4 show that the peptide of the present invention exhibited greater translocation capability than previous peptides in peripheral mononuclear cells.

Experimental Example 4

Cellular and Nuclear Translocation Capability of Quantum Dots in HeLa Cells

Cellular and nuclear translocation testing of LR15DL-Qdot (Conjugate 14) synthesized in Example 12 was performed by the following method.

The LR15DL-Qdot conjugate (Conjugate 14) obtained in Example 12 was added to $4 \times 10^6$ HeLa cells wherein the cell cycle had been arrested by thymidine to make a final concentration of 6 nM. After 16 h the cells were washed three times with PBS and the cells were detached and collected with a scraper. The cells were washed once with PBS, lysed with a Dounce homogenizer, and precipitated by centrifugation (2000 rpm for 5 min). The supernatant was the cytoplasmic fraction and the pellets were the nuclear fraction (the pellets were sonicated after adding 0.5% Triton X-100/PBS solution). The fluorescent intensity of each resulting fraction was then measured. The fluorescent intensity of the fractions was measured under conditions of an excitation wavelength of 350 nm and a fluorescence wavelength of 700 nm. The results are shown in FIG. 5.

Figure 5:
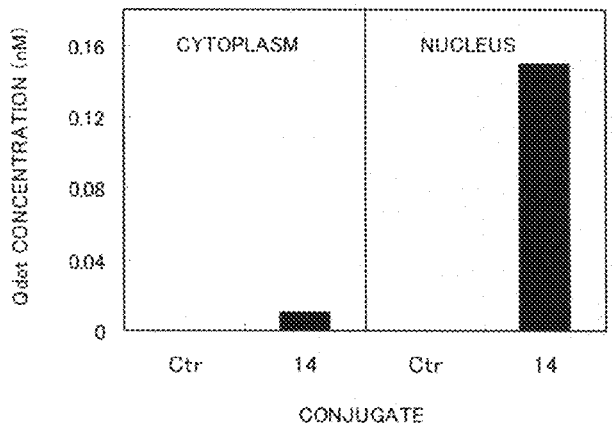
FIG. 5 is a graph showing the results of cellular and nuclear translocation capability of the LR15DL-Qdot conjugate in HeLa cells.

The results of FIG. 5 confirm that even when a Qdot® was selected as the cargo substance, cellular and nuclear translocation occurred in the same manner.

Experimental Example 5

Cellular Translocation Capability of a Protein 1

Cellular translocation testing of LR15DL-EGFP (Conjugate 15) synthesized in Example 13 was performed in the following manner.

LR15DL-EGFP (Conjugate 15) obtained in Example 13 was added to HEK293T cells to make a concentration of 10 µg/mL and incubated for 4 h at 37° C. Then the cells were trypsinized and the amount of cells fluorescing due to EGFP uptake was measured using FACS (Fluorescence Activated Cell Sorting) analysis. The results are shown in FIG. 6.

Figure 6:
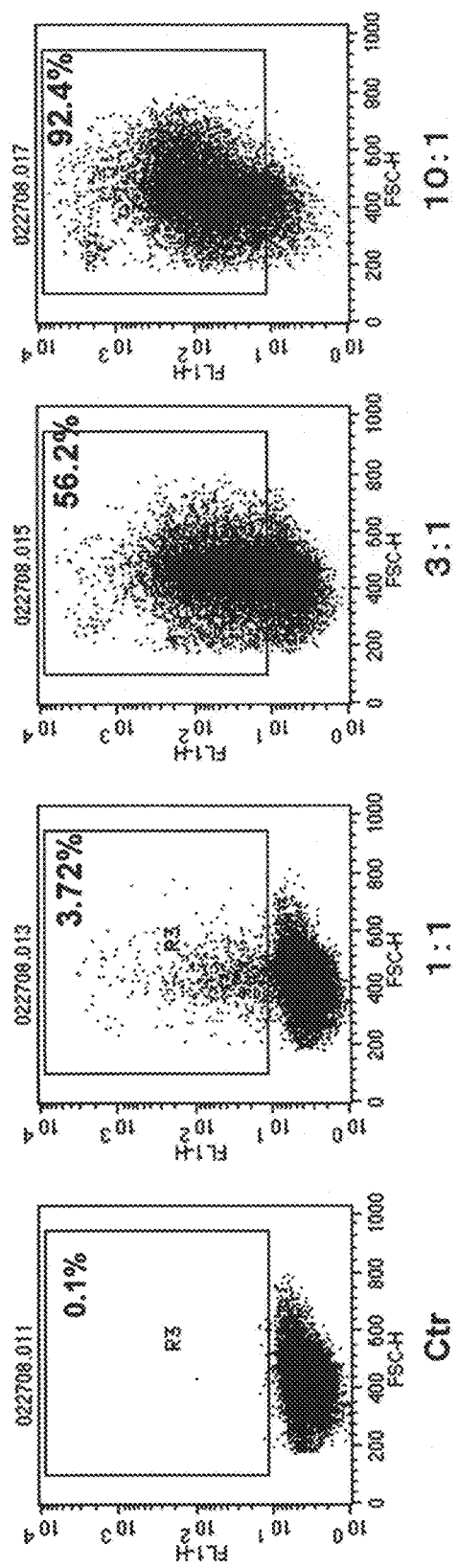
FIG. 6 shows FACS analysis diagrams illustrating cellular translocation test results for the LR15DL-EGFP conjugate in HEK293T cells.

The results of FIG. 6 confirmed that the peptide of the present invention is capable of cellular translocation of a peptide. The results also indicated that the translocation capability is dependent on the peptide bonding amount.

Experimental Example 6

Cellular Translocation Capability of a Protein 2

Cellular translocation testing of the $(His)_6$-LR15DL-EGFP chimeric protein (Conjugate 16) synthesized in Example 14 was performed in the following manner.

First the $(His)_6$-LR15DL-EGFP (Conjugate 16) obtained in Example 14 was added to HEK293T cells to make a concentration of 17.5 µg/mL and after incubation at 37° C. for 4 h, the cells were washed to remove the excess conjugate. On the following day the cells were detached from the substrate with trypsin, and the amount of cells fluorescing due to EGFP uptake was measured by FACS analysis. The results are shown in FIG. 7.

Figure 7:
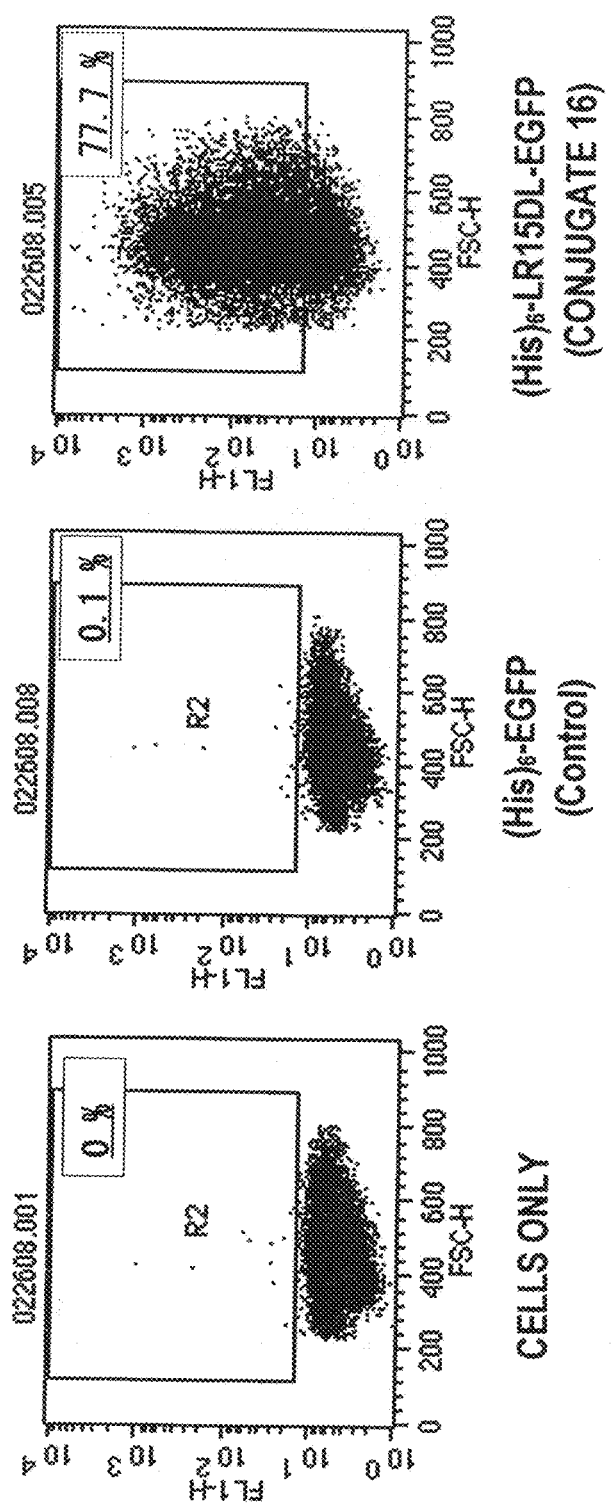
FIG. 7 shows FACS analysis diagrams illustrating cellular translocation test results for the $(His)_6$-LR15DL-EGFP chimeric protein in HEK293T cells.

The results of FIG. 7 confirmed that a chimeric protein incorporating the amino acid sequence of the peptide of the present invention has cellular translocation capability.

Experimental Example 7

Cytotoxicity Test

Testing of the peptide of the present invention for damage to intracellular DNA was performed in the following manner.

(Day 1) HeLa cells were seeded onto a dish at a concentration of 5×10$^4$ cells/dish, and cultured in 10% FCS/DMEM medium (2 mL).

(Day 2) Recombinant Vpr (protein derived from Vpr), C45D18 (Peptide 9), and LR20 (Peptide 1) were added, and the cells were incubated for 2 days.

(Day 4) The following sequence of treatments was performed on the cells: The dish was washed with PBS→the cells were fixed with 4% paraformaldehyde→after incubation for 20 min on ice, the cells were washed with PBS→200 μL of 1% Triton X-100/2M HCl solution was added, and the cells were incubated at room temperature for 30 min→blocking with 200 μL of 1% BSA was performed at room temperature for 1 h→anti-γ-H2AX antibody solution was added, and the fragmented double-stranded DNA was stained (37° C. for 30 min)→cy3-anti-mouse IgG solution was added, and the cells were incubated at room temperature for 30 min→the nuclei were stained with DAPI/PBST (3 min)→the cells were mounted on glass slides.

Figure 8:
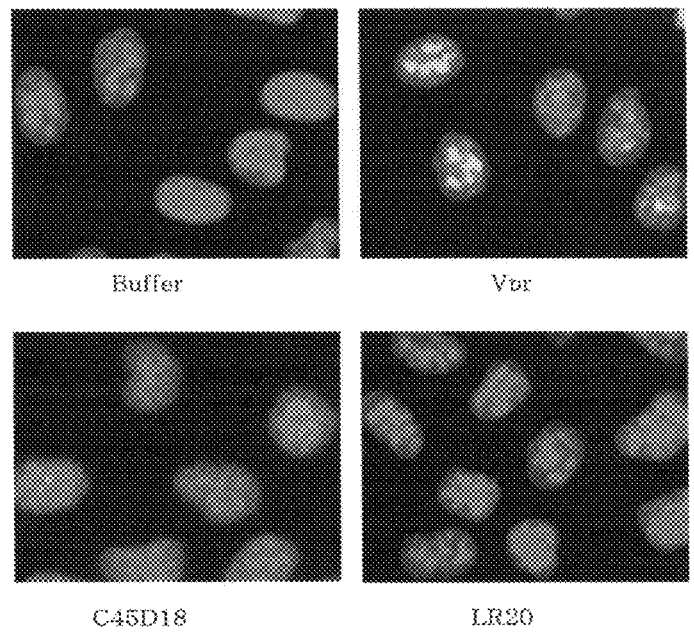
FIG. 8 shows micrographs comparing cytotoxicity test results for LR20, C45D18, and Vpr.

The results are shown in FIG. 8. In FIG. 8 the stained parts indicate fragmented DNA.

The results of FIG. 8 show that the extent of DNA damage is decreased with LR20, which is a typical example of the group of peptides of the present invention. Legend: upper left=buffer control, upper right=recombinant Vpr, lower left=C45D18, lower right=LR20.

A similar test was performed for LR15DL, and it was confirmed that no damage to DNA was seen.

Experimental Example 8

Figure 9:
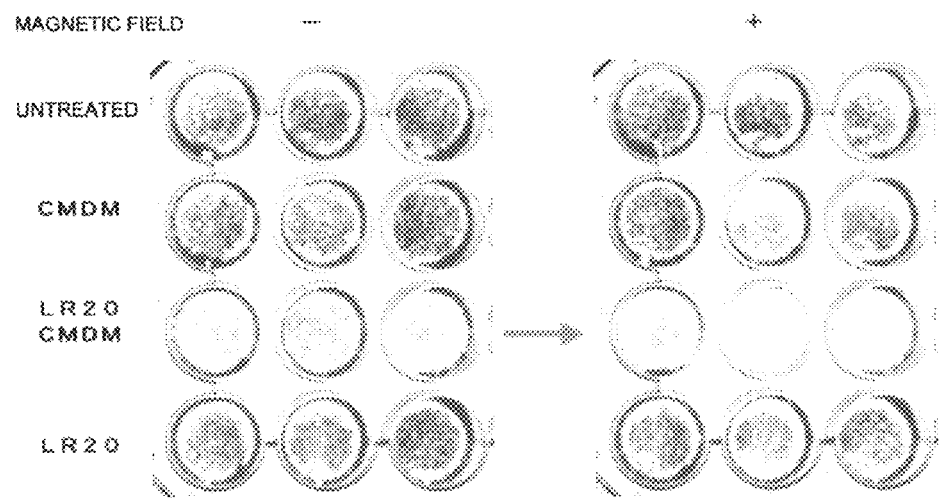
FIG. 9 shows photographs of Petri dishes containing stained cells, illustrating the results when cell viability was investigated after cells that had taken up the LR20-CMDM conjugate were exposed to a high frequency magnetic field.

High Frequency Magnetic Field Treatment of Cells that Took Up the Peptide-Magnetic Nanoparticle Conjugate of the Present Invention The LR20-CMDM (Conjugate 1) obtained in Example 1 and the CMDM and LR20 peptide monomer starting materials thereof were added to HeLa cells at an iron concentration of 800 μg/mL and incubated for 12 h. Then the cells were exposed for 1 h to a high frequency magnetic field with a frequency of 350 kHz and a magnetic strength of 21 mT. FIG. 9 shows the state of cell growth on day 3 thereafter. The stained parts indicate live cells.

From the results of FIG. 9 it can be seen that the LR20-CMDM conjugate tends to impart damage to cells as a result of magnetic field exposure.

Industrial Applicability

The peptide can be used as a transformation vector by bonding the same to a nucleic acid for the purpose of genetic modification.

The peptide can be used as a DDS to targeted cells by bonding the same to a drug or drug inclusion compound.

The peptide can be used for molecular imaging, magnetic labeling of cells, or treatment with a high frequency magnetic field treatment to kill cancer cells by bonding the same to a magnetic particle capable of MRI imaging and generating heat due to magnetic field exposure.

---

The invention claimed is:

1. A peptide, consisting of SEQ ID NO: 1 or SEQ ID NO: 3.

2. The peptide according to claim 1, used as a vector for transport of a biologically active substance into a cell or a nucleus.

3. A conjugate, wherein the peptide according to claim 1 is joined directly, or indirectly to a functional molecule via a linker molecule.

4. The conjugate according to claim 3, wherein the functional molecule is a biologically active substance selected from a group consisting of nucleic acids, amino acids, lipids, sugars, and other polymer compounds.

5. The conjugate according to claim 3, wherein the functional molecule is a magnetic nanoparticle or a liposome.

6. The peptide of claim 1, consisting of the amino acid sequence of SEQ ID NO:1.

7. The peptide of claim 1, consisting of the amino acid sequence of SEQ ID NO:3.

* * * * *

UNITED STATES PATENT AND TRADEMARK OFFICE
CERTIFICATE OF CORRECTION

PATENT NO. : 8,455,616 B2
APPLICATION NO. : 12/450010
DATED : June 4, 2013
INVENTOR(S) : Ishizaka et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 872 days.

Signed and Sealed this
Eighth Day of September, 2015

Michelle K. Lee
*Director of the United States Patent and Trademark Office*

SEQUENCE LISTING

<160> NUMBER OF SEQ ID NOS: 31

<210> SEQ ID NO 1
<211> LENGTH: 10
<212> TYPE: PRT
<213> ORGANISM: Artificial sequence
<220> FEATURE:
<223> OTHER INFORMATION: Synthetic construct; modified partial sequence
      of Vpr from HIV-1

<400> SEQUENCE: 1

Arg Ile Phe Ile His Phe Arg Ile Gly Cys
1               5                   10

<210> SEQ ID NO 2
<211> LENGTH: 15
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 2

Arg Ile Xaa Gln Gln Xaa Xaa Phe Ile His Phe Arg Ile Gly Cys
1               5                   10                  15

<210> SEQ ID NO 3
<211> LENGTH: 8
<212> TYPE: PRT
<213> ORGANISM: Artificial sequence

```
<220> FEATURE:
<223> OTHER INFORMATION: Synthetic construct; modified partial sequence
      of Vpr from HIV-1

<400> SEQUENCE: 3

Arg Ile Phe Ile Arg Ile Gly Cys
1               5

<210> SEQ ID NO 4
<211> LENGTH: 30
<212> TYPE: RNA
<213> ORGANISM: Artificial sequence
<220> FEATURE:
<223> OTHER INFORMATION: Synthetic construct; encodes LR15DL amino acid
      sequence
<220> FEATURE:
<221> NAME/KEY: CDS
<222> LOCATION: (1)..(30)
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (27)..(27)
<223> OTHER INFORMATION: n is a, c, g, or u

<400> SEQUENCE: 4 mgn auh uuy auh cay uuy mgn auh ggn ugy                           30
Arg Xaa Xaa Xaa His Xaa Arg Xaa Gly Xaa
1               5                   10

<210> SEQ ID NO 5
<211> LENGTH: 10
<212> TYPE: PRT
<213> ORGANISM: Artificial sequence
<220> FEATURE:
<221> NAME/KEY: misc_feature
<222> LOCATION: (2)..(2)
<223> OTHER INFORMATION: The 'Xaa' at location 2 stands for Ile.
<220> FEATURE:
<221> NAME/KEY: misc_feature
<222> LOCATION: (3)..(3)
<223> OTHER INFORMATION: The 'Xaa' at location 3 stands for Phe.
<220> FEATURE:
<221> NAME/KEY: misc_feature
<222> LOCATION: (4)..(4)
<223> OTHER INFORMATION: The 'Xaa' at location 4 stands for Ile.
<220> FEATURE:
<221> NAME/KEY: misc_feature
<222> LOCATION: (6)..(6)
<223> OTHER INFORMATION: The 'Xaa' at location 6 stands for Phe.
<220> FEATURE:
<221> NAME/KEY: misc_feature
<222> LOCATION: (8)..(8)
<223> OTHER INFORMATION: The 'Xaa' at location 8 stands for Ile.
<220> FEATURE:
<221> NAME/KEY: misc_feature
<222> LOCATION: (10)..(10)
<223> OTHER INFORMATION: The 'Xaa' at location 10 stands for Cys.
<220> FEATURE:
<223> OTHER INFORMATION: Synthetic Construct

<400> SEQUENCE: 5

Arg Xaa Xaa Xaa His Xaa Arg Xaa Gly Xaa
1               5                   10

<210> SEQ ID NO 6
<211> LENGTH: 45
<212> TYPE: RNA
```

-continued

```
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(45)
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (7)..(9)
<223> OTHER INFORMATION: n is a, c, g, or u
<220> FEATURE:
<221> NAME/KEY: misc_feature
<222> LOCATION: (16)..(21)
<223> OTHER INFORMATION: n is a, c, g, or u
<220> FEATURE:
<221> NAME/KEY: misc_feature
<222> LOCATION: (36)..(36)
<223> OTHER INFORMATION: n is a, c, g, or u
<220> FEATURE:
<221> NAME/KEY: misc_feature
<222> LOCATION: (42)..(42)
<223> OTHER INFORMATION: n is a, c, g, or u

<400> SEQUENCE: 6 mgn auh nnn car car nnn nnn uuy auh cay uuy mgn auh ggn ugy      45
Arg Xaa Xaa Gln Gln Xaa Xaa Xaa Xaa His Xaa Arg Xaa Gly Xaa
 1               5                  10                  15

<210> SEQ ID NO 7
<211> LENGTH: 15
<212> TYPE: PRT
<213> ORGANISM: Artificial sequence
<220> FEATURE:
<221> NAME/KEY: misc_feature
<222> LOCATION: (2)..(2)
<223> OTHER INFORMATION: The 'Xaa' at location 2 stands for Ile.
<220> FEATURE:
<221> NAME/KEY: misc_feature
<222> LOCATION: (3)..(3)
<223> OTHER INFORMATION: The 'Xaa' at location 3 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (6)..(6)
<223> OTHER INFORMATION: The 'Xaa' at location 6 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (7)..(7)
<223> OTHER INFORMATION: The 'Xaa' at location 7 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (8)..(8)
<223> OTHER INFORMATION: The 'Xaa' at location 8 stands for Phe.
<220> FEATURE:
<221> NAME/KEY: misc_feature
<222> LOCATION: (9)..(9)
<223> OTHER INFORMATION: The 'Xaa' at location 9 stands for Ile.
<220> FEATURE:
<221> NAME/KEY: misc_feature
<222> LOCATION: (11)..(11)
<223> OTHER INFORMATION: The 'Xaa' at location 11 stands for Phe.
<220> FEATURE:
<221> NAME/KEY: misc_feature
<222> LOCATION: (13)..(13)
<223> OTHER INFORMATION: The 'Xaa' at location 13 stands for Ile.
<220> FEATURE:
<221> NAME/KEY: misc_feature
<222> LOCATION: (15)..(15)
<223> OTHER INFORMATION: The 'Xaa' at location 15 stands for Cys.
```

```
<220> FEATURE:
<223> OTHER INFORMATION: Synthetic Construct

<400> SEQUENCE: 7

Arg Xaa Xaa Gln Gln Xaa Xaa Xaa Xaa His Xaa Arg Xaa Gly Xaa
 1               5                  10                  15

<210> SEQ ID NO 8
<211> LENGTH: 24
<212> TYPE: RNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(24)
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u
<220> FEATURE:
<221> NAME/KEY: misc_feature
<222> LOCATION: (21)..(21)
<223> OTHER INFORMATION: n is a, c, g, or u

<400> SEQUENCE: 8 mgn auh uuy auh mgn auh ggn ugy                                       24
Arg Xaa Xaa Xaa Arg Xaa Gly Xaa
 1               5

<210> SEQ ID NO 9
<211> LENGTH: 8
<212> TYPE: PRT
<213> ORGANISM: Artificial sequence
<220> FEATURE:
<221> NAME/KEY: misc_feature
<222> LOCATION: (2)..(2)
<223> OTHER INFORMATION: The 'Xaa' at location 2 stands for Ile.
<220> FEATURE:
<221> NAME/KEY: misc_feature
<222> LOCATION: (3)..(3)
<223> OTHER INFORMATION: The 'Xaa' at location 3 stands for Phe.
<220> FEATURE:
<221> NAME/KEY: misc_feature
<222> LOCATION: (4)..(4)
<223> OTHER INFORMATION: The 'Xaa' at location 4 stands for Ile.
<220> FEATURE:
<221> NAME/KEY: misc_feature
<222> LOCATION: (6)..(6)
<223> OTHER INFORMATION: The 'Xaa' at location 6 stands for Ile.
<220> FEATURE:
<221> NAME/KEY: misc_feature
<222> LOCATION: (8)..(8)
<223> OTHER INFORMATION: The 'Xaa' at location 8 stands for Cys.
<220> FEATURE:
<223> OTHER INFORMATION: Synthetic Construct

<400> SEQUENCE: 9

Arg Xaa Xaa Xaa Arg Xaa Gly Xaa
 1               5

<210> SEQ ID NO 10
<211> LENGTH: 30
<212> TYPE: RNA
<213> ORGANISM: Artificial sequence
<220> FEATURE:
<223> OTHER INFORMATION: Synthetic construct; encodes LR15DL amino acid
      sequence
<220> FEATURE:
<221> NAME/KEY: misc_feature
```

```
<222> LOCATION: (1)..(30)
<220> FEATURE:
<221> NAME/KEY: CDS
<222> LOCATION: (1)..(30)
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (27)..(27)
<223> OTHER INFORMATION: n is a, c, g, or u

<400> SEQUENCE: 10 mgn auh uuy auh cay uuy mgn auh ggn ugy                     30
Arg Xaa Xaa Xaa His Xaa Arg Xaa Gly Xaa
1               5                   10

<210> SEQ ID NO 11
<211> LENGTH: 10
<212> TYPE: PRT
<213> ORGANISM: Artificial sequence
<220> FEATURE:
<221> NAME/KEY: misc_feature
<222> LOCATION: (2)..(2)
<223> OTHER INFORMATION: The 'Xaa' at location 2 stands for Ile.
<220> FEATURE:
<221> NAME/KEY: misc_feature
<222> LOCATION: (3)..(3)
<223> OTHER INFORMATION: The 'Xaa' at location 3 stands for Phe.
<220> FEATURE:
<221> NAME/KEY: misc_feature
<222> LOCATION: (4)..(4)
<223> OTHER INFORMATION: The 'Xaa' at location 4 stands for Ile.
<220> FEATURE:
<221> NAME/KEY: misc_feature
<222> LOCATION: (6)..(6)
<223> OTHER INFORMATION: The 'Xaa' at location 6 stands for Phe.
<220> FEATURE:
<221> NAME/KEY: misc_feature
<222> LOCATION: (8)..(8)
<223> OTHER INFORMATION: The 'Xaa' at location 8 stands for Ile.
<220> FEATURE:
<221> NAME/KEY: misc_feature
<222> LOCATION: (10)..(10)
<223> OTHER INFORMATION: The 'Xaa' at location 10 stands for Cys.
<220> FEATURE:
<223> OTHER INFORMATION: Synthetic Construct

<400> SEQUENCE: 11

Arg Xaa Xaa Xaa His Xaa Arg Xaa Gly Xaa
1               5                   10

<210> SEQ ID NO 12
<211> LENGTH: 45
<212> TYPE: RNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(45)
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (7)..(9)
<223> OTHER INFORMATION: n is a, c, g, or u
<220> FEATURE:
<221> NAME/KEY: misc_feature
```

```
<222> LOCATION: (16)..(21)
<223> OTHER INFORMATION: n is a, c, g, or u
<220> FEATURE:
<221> NAME/KEY: misc_feature
<222> LOCATION: (36)..(36)
<223> OTHER INFORMATION: n is a, c, g, or u
<220> FEATURE:
<221> NAME/KEY: misc_feature
<222> LOCATION: (42)..(42)
<223> OTHER INFORMATION: n is a, c, g, or u

<400> SEQUENCE: 12 mgn auh nnn car car nnn nnn uuy auh cay uuy mgn auh ggn ugy        45
Arg Xaa Xaa Gln Gln Xaa Xaa Xaa Xaa His Xaa Arg Xaa Gly Xaa
1               5                   10                  15

<210> SEQ ID NO 13
<211> LENGTH: 15
<212> TYPE: PRT
<213> ORGANISM: Artificial sequence
<220> FEATURE:
<221> NAME/KEY: misc_feature
<222> LOCATION: (2)..(2)
<223> OTHER INFORMATION: The 'Xaa' at location 2 stands for Ile.
<220> FEATURE:
<221> NAME/KEY: misc_feature
<222> LOCATION: (3)..(3)
<223> OTHER INFORMATION: The 'Xaa' at location 3 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (6)..(6)
<223> OTHER INFORMATION: The 'Xaa' at location 6 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (7)..(7)
<223> OTHER INFORMATION: The 'Xaa' at location 7 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (8)..(8)
<223> OTHER INFORMATION: The 'Xaa' at location 8 stands for Phe.
<220> FEATURE:
<221> NAME/KEY: misc_feature
<222> LOCATION: (9)..(9)
<223> OTHER INFORMATION: The 'Xaa' at location 9 stands for Ile.
<220> FEATURE:
<221> NAME/KEY: misc_feature
<222> LOCATION: (11)..(11)
<223> OTHER INFORMATION: The 'Xaa' at location 11 stands for Phe.
<220> FEATURE:
<221> NAME/KEY: misc_feature
<222> LOCATION: (13)..(13)
<223> OTHER INFORMATION: The 'Xaa' at location 13 stands for Ile.
<220> FEATURE:
<221> NAME/KEY: misc_feature
<222> LOCATION: (15)..(15)
<223> OTHER INFORMATION: The 'Xaa' at location 15 stands for Cys.
<220> FEATURE:
<223> OTHER INFORMATION: Synthetic Construct

<400> SEQUENCE: 13

Arg Xaa Xaa Gln Gln Xaa Xaa Xaa Xaa His Xaa Arg Xaa Gly Xaa
1               5                   10                  15

<210> SEQ ID NO 14
<211> LENGTH: 24
<212> TYPE: RNA
<213> ORGANISM: Artificial sequence
<220> FEATURE:
<223> OTHER INFORMATION: Synthetic construct; encodes LR8DHF amino acid
      sequence
```

```
<220> FEATURE:
<221> NAME/KEY: misc_feature
<222> LOCATION: (1)..(24)
<220> FEATURE:
<221> NAME/KEY: CDS
<222> LOCATION: (1)..(24)
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u
<220> FEATURE:
<221> NAME/KEY: misc_feature
<222> LOCATION: (21)..(21)
<223> OTHER INFORMATION: n is a, c, g, or u

<400> SEQUENCE: 14 mgn auh uuy auh mgn auh ggn ugy                                   24
Arg Xaa Xaa Xaa Arg Xaa Gly Xaa
1               5

<210> SEQ ID NO 15
<211> LENGTH: 8
<212> TYPE: PRT
<213> ORGANISM: Artificial sequence
<220> FEATURE:
<221> NAME/KEY: misc_feature
<222> LOCATION: (2)..(2)
<223> OTHER INFORMATION: The 'Xaa' at location 2 stands for Ile.
<220> FEATURE:
<221> NAME/KEY: misc_feature
<222> LOCATION: (3)..(3)
<223> OTHER INFORMATION: The 'Xaa' at location 3 stands for Phe.
<220> FEATURE:
<221> NAME/KEY: misc_feature
<222> LOCATION: (4)..(4)
<223> OTHER INFORMATION: The 'Xaa' at location 4 stands for Ile.
<220> FEATURE:
<221> NAME/KEY: misc_feature
<222> LOCATION: (6)..(6)
<223> OTHER INFORMATION: The 'Xaa' at location 6 stands for Ile.
<220> FEATURE:
<221> NAME/KEY: misc_feature
<222> LOCATION: (8)..(8)
<223> OTHER INFORMATION: The 'Xaa' at location 8 stands for Cys.
<220> FEATURE:
<223> OTHER INFORMATION: Synthetic Construct

<400> SEQUENCE: 15

Arg Xaa Xaa Xaa Arg Xaa Gly Xaa
1               5

<210> SEQ ID NO 16
<211> LENGTH: 27
<212> TYPE: PRT
<213> ORGANISM: Artificial Sequence
<220> FEATURE:
<223> OTHER INFORMATION: C45D18 peptide

<400> SEQUENCE: 16

Asp Thr Trp Ala Gly Val Glu Ala Ile Ile Arg Ile Leu Gln Gln Leu
1               5                   10                  15

Leu Phe Ile His Phe Arg Ile Gly Cys Arg His
            20                  25

<210> SEQ ID NO 17
<211> LENGTH: 4
<212> TYPE: PRT
<213> ORGANISM: Artificial Sequence
<220> FEATURE:
```

```
<223> OTHER INFORMATION: Sequence motif of claimed peptides

<400> SEQUENCE: 17

Arg Ile Gly Cys
1

<210> SEQ ID NO 18
<211> LENGTH: 20
<212> TYPE: PRT
<213> ORGANISM: Artificial Sequence
<220> FEATURE:
<223> OTHER INFORMATION: LR20 peptide

<400> SEQUENCE: 18

Arg Ile Leu Gln Gln Leu Leu Phe Ile His Phe Arg Ile Gly Cys Arg
1               5                   10                  15

His Ser Arg Ile
            20

<210> SEQ ID NO 19
<211> LENGTH: 17
<212> TYPE: PRT
<213> ORGANISM: Artificial Sequence
<220> FEATURE:
<223> OTHER INFORMATION: LR17 peptide

<400> SEQUENCE: 19

Arg Ile Leu Gln Gln Leu Leu Phe Ile His Phe Arg Ile Gly Cys Arg
1               5                   10                  15

His

<210> SEQ ID NO 20
<211> LENGTH: 15
<212> TYPE: PRT
<213> ORGANISM: Artificial Sequence
<220> FEATURE:
<223> OTHER INFORMATION: LR15 peptide

<400> SEQUENCE: 20

Arg Ile Leu Gln Gln Leu Leu Phe Ile His Phe Arg Ile Gly Cys
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: LR11 peptide

<400> SEQUENCE: 21

Arg Ile Leu Gln Gln Leu Leu Phe Ile His Phe
1               5                   10

<210> SEQ ID NO 22
<211> LENGTH: 6
<212> TYPE: PRT
<213> ORGANISM: Artificial Sequence
<220> FEATURE:
<223> OTHER INFORMATION: LR8DHFRI peptide

<400> SEQUENCE: 22

Arg Ile Phe Ile Gly Cys
1               5

<210> SEQ ID NO 23
<211> LENGTH: 6
```

```
<212> TYPE: PRT
<213> ORGANISM: Artificial Sequence
<220> FEATURE:
<223> OTHER INFORMATION: LR8DRIHF peptide

<400> SEQUENCE: 23

Phe Ile Arg Ile Gly Cys
1               5

<210> SEQ ID NO 24
<211> LENGTH: 16
<212> TYPE: PRT
<213> ORGANISM: Artificial Sequence
<220> FEATURE:
<223> OTHER INFORMATION: Penetratin peptide

<400> SEQUENCE: 24

Arg Gln Ile Lys Ile Trp Phe Gln Asn Arg Arg Met Lys Trp Lys Lys
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: Tat(46-57) peptide

<400> SEQUENCE: 25

Gly Tyr Gly Arg Lys Lys Arg Arg Gly Arg Arg Arg
1               5                   10

<210> SEQ ID NO 26
<211> LENGTH: 11
<212> TYPE: PRT
<213> ORGANISM: Artificial Sequence
<220> FEATURE:
<223> OTHER INFORMATION: YM-3 peptide

<400> SEQUENCE: 26

Thr His Arg Leu Pro Arg Arg Arg Arg Arg Arg
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Sequence element of claimed peptides

<400> SEQUENCE: 27

Phe Ile His Phe Arg Ile Gly Cys
1               5

<210> SEQ ID NO 28
<211> LENGTH: 5
<212> TYPE: PRT
<213> ORGANISM: Artificial Sequence
<220> FEATURE:
<223> OTHER INFORMATION: Sequence element of claimed peptides
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 28
```

```
Xaa Gln Gln Xaa Xaa
1               5

<210> SEQ ID NO 29
<211> LENGTH: 30
<212> TYPE: DNA
<213> ORGANISM: Artificial Sequence
<220> FEATURE:
<223> OTHER INFORMATION: DNA sequence encoding LR15DL

<400> SEQUENCE: 29
aggatcttca tccacttccg gatcggctgc                                      30

<210> SEQ ID NO 30
<211> LENGTH: 5
<212> TYPE: PRT
<213> ORGANISM: Artificial Sequence
<220> FEATURE:
<223> OTHER INFORMATION: Sequence element of LR20 peptide

<400> SEQUENCE: 30

Arg His Ser Arg Ile
1               5

<210> SEQ ID NO 31
<211> LENGTH: 5
<212> TYPE: PRT
<213> ORGANISM: Artificial Sequence
<220> FEATURE:
<223> OTHER INFORMATION: Sequence element of claimed peptides

<400> SEQUENCE: 31

Leu Gln Gln Leu Leu
1               5
```